US006555548B2

(12) United States Patent
McCall et al.

(10) Patent No.: US 6,555,548 B2
(45) Date of Patent: Apr. 29, 2003

(54) COMPOUNDS FOR TREATING FIBROMYALGIA AND CHRONIC FATIGUE SYNDROME

(75) Inventors: Robert B. McCall, Kalamazoo, MI (US); Robert Clyde Marshall, Mattawan, MI (US); David W. Robertson, Galesburg, MI (US); Thomas M. Ashley, Portage, MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

(21) Appl. No.: 10/159,913

(22) Filed: May 30, 2002

(65) Prior Publication Data

US 2002/0143010 A1 Oct. 3, 2002

Related U.S. Application Data

(62) Division of application No. 09/836,660, filed on Apr. 17, 2001, now Pat. No. 6,448,258.
(60) Provisional application No. 60/198,959, filed on Apr. 21, 2000, and provisional application No. 60/200,569, filed on Apr. 28, 2000.

(51) Int. Cl.⁷ .............................................. A61K 31/437
(52) U.S. Cl. ....................................................... 514/288
(58) Field of Search ......................................... 514/288

(56) References Cited

U.S. PATENT DOCUMENTS

| | | | |
|---|---|---|---|
| 4,526,892 A | 7/1985 | Salvati et al. | 514/288 |
| 5,273,975 A | 12/1993 | Moon et al. | 514/233.2 |
| 5,436,240 A | 7/1995 | Moon et al. | 514/224.5 |
| 5,462,947 A | 10/1995 | Svensson et al. | 514/317 |
| 5,594,024 A | 1/1997 | Svensson et al. | 514/429 |

FOREIGN PATENT DOCUMENTS

| | | |
|---|---|---|
| DE | 19938823 | 2/2001 |
| WO | WO90/15058 | 12/1990 |
| WO | WO95/04056 A | 2/1995 |
| WO | WO00/40226 | 7/2000 |
| WO | WO01/01973 | 1/2001 |
| WO | WO01/15677 | 3/2001 |

OTHER PUBLICATIONS

Patent Abstracts of Japan, vol. 1998, No. 6, Apr. 30, 1998 (JP 10053525).

Gould, Philip L., *Salt Selection for Basic Drugs, International Journal of pharmaceutics.* vol. 33, pp. 201–217, 1986.

*Primary Examiner*—Phyllis G. Spivack
(74) *Attorney, Agent, or Firm*—Austin W. Zhang

(57) ABSTRACT

The present invention provides for methods for the treatment of fibromyalgia syndrome or chronic fatigue syndrome by the administration of cabergoline-type compounds or a salt of said compound.

4 Claims, No Drawings

COMPOUNDS FOR TREATING FIBROMYALGIA AND CHRONIC FATIGUE SYNDROME

CROSS-REFERENCE TO RELATED APPLICATIONS

The present application is a divisional application of U.S. patent application Ser. No. 09/836,660, filed Apr. 17, 2001, now U.S. Pat. No. 6,448,758, which in turn claims the benefit of Ser. Nos. 60/198,959 filed Apr. 21, 2000 and 60/200,569 filed Apr. 28, 2000.

FIELD OF THE INVENTION

The present invention relates to the use of neuromuscular agents, and the pharmacologically acceptable salts thereof, for the treatment of nervous system disorders, and more particularly to the use of compounds of U.S. Pat. Nos. 5,273,975, 5,436,240, 5,594,024, 5,462,947, and 4,526,892 for the treatment of symptoms of fibromyalgia syndrome and chronic fatigue syndrome.

BACKGROUND OF THE INVENTION

Chronic fatigue syndrome (CFS), also referred to as chronic fatigue immune disorders syndrome, yuppie flu; fatigue—chronic, and chronic fatigue and immune dysfunction syndrome, is a clinically defined condition characterized by profound tiredness or fatigue. In addition, patients with CFS generally report various nonspecific symptoms, including weakness, muscle aches and pains, excessive sleep, malaise, fever, sore throat, tender lymph nodes, impaired memory and/or mental concentration, insomnia, and depression. The exact cause of CFS is unknown and, to date, there are no specific tests to confirm the diagnosis of CFS, though a variety of tests are usually done to exclude other possible causes of the symptoms.

Fibromyalgia syndrome (FMS), also referred to as fibromyalgia, fibromyositis, fibrositis, or myofasical pain syndrome, is a rheumatic condition generally characterized by widespread pain in fibrous tissues, muscles, tendons, and other connective tissues, fatigue, headaches, lack of restorative sleep, and numbness. Thus, FMS shares many clinical features with CFS. Similar to CFS, there are no specific diagnostic tests for FMS.

Many medications are commonly used to treat CFS and FMS. Examples of the more common medications include hypnotics, immune suppressants, various other prescribed medications, and an array of non-prescription medications. Examples of other prescription drugs include opioid antagonists, sodium retention agents/beta blockers, calcium channel blockers/histamine blockers, anti-depressants, allergy medications, and acute anxiety medications. However, there are no known medications that permanently resolve the symptoms of either CFS or FMS. In addition, many of the currently used medications produce side effects ranging from mild side effects, e.g., drowsiness, dizziness, and nausea to serious side effects, e.g., addiction and liver damage Accordingly, there is clearly a need for better treatments for chronic fatigue syndrome and fibromyalgia. Now, the present invention reveals several compounds that can be formulated into useful therapeutic treatments for these conditions.

SUMMARY OF THE INVENTION

Disclosed is a method of treating symptoms of fibromyalgia syndrome or chronic fatigue syndrome which comprises administering to a patient in need of treatment a therapeutically effective amount of a heterocyclic amine-type compound of formula (A),

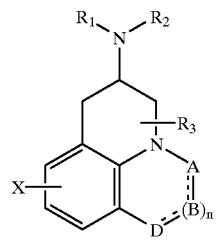

Formula (A)

or a pharmaceutically acceptable salt thereof, wherein:

$R_1$, $R_2$, and $R_3$ are independently hydrogen, $C_{1-6}$ alkyl, $C_{3-5}$ alkenyl, $C_{3-5}$ alkynyl, $C_{3-7}$ cycloalkyl, $C_{4-10}$ cycloalkyl or phenyl-substituted $C_{1-6}$ alkyl, or $R_1$ and $R_2$ are joined to form a $C_{3-7}$ cyclic amine which can contain additional heteroatoms and/or unsaturation;

X is hydrogen, $C_{1-6}$ alkyl, halogen, hydroxy, alkoxy, cyano, carboxamide, carboxyl, or carboalkoxyl;

A is CH, $CH_2$, CH-halogen, $CHCH_3$, C=O, C=S, C—$SCH_3$, C=NH, C—$NH_2$, C—$NHCH_3$, C—$NHCOOCH_3$, C—NHCN, $SO_2$, or N;

B is $CH_2$, CH, CH-halogen, C=O, N, NH or N—$CH_3$, or O;

n is 0 or 1; and

D is CH, $CH_2$, CH-halogen, C=O, O, N, NH, or N—$CH_3$.

Preferred compounds of formula (A) include (R)-5,6-Dihydro-5-(methylamino)-4H-imidazo[4,5,1-ij]-quinolin-2(1H)-one (uninverted CAS name) and (5R)-5-(methylamino)-5,6-dihydro-4H-imidazo[4,5,1-ij]quinoline-2(1H)-thione, and their pharmaceutically acceptable salts. Also disclosed is a method of treating symptoms of fibromyalgia syndrome or chronic fatigue syndrome which comprises administering to a patient in need of treatment a therapeutically effective amount of a substituted phenylazacycloalkane-type compound of formula (B),

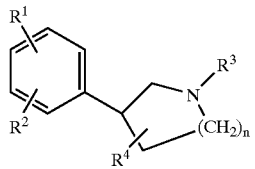

Formula (B)

or pharmaceutically acceptable salts thereof, wherein:

n is 0–3;

$R^1$ and $R^2$ are independently H (provided only one is H at the same time), —OH (provided $R^4$ is other than hydrogen), CN, $CH_2CN$, 2- or 4-$CF_3$, $CH_2CF_3$, $CH_2CHF_2$, CH=$CF_2$ $_{(CH2)_2}CF_3$, ethenyl, 2-propenyl, $OSO_2CH_3$, $OSO_2CF_3$, $SSO_2CF_3$, $COR^4$, $COOR^4$, CON$(R^4)_2$, $SO_xCH_3$ (where, x is 0–2), $SO_xCF_3$, $O(CH_2)_xCF_3$, $SO_2N($ $COCOOR^4$, $COCOON(R^4)_2$, $C_{1-8}$ alkyls, $C_{3-8}$ cycloalkyls, $CH_2OR^4$, $CH_2(R^4)_2$, $NR^4SO_2CF_3$, $NO_2$, halogen, a phenyl at positions 2, 3 or 4, thienyl, furyl, pyrrole, oxazole, thiazole, N-pyrroline, triazole, tetrazole or pyridine;

$R^3$ is hydrogen, $CF_3$, $CH_2CF_3$, $C_1$–$C_8$ alkyl, $C_3$–$C_8$ cycloalkyl, $C_4$–$C_9$ cycloalkyl-methyl, $C_2$–$C_8$ alkenyl, $C_2$–$C_8$ alkynyl, 3,3,3-trifluoropropyl, 4,4,4-trifluorobutyl, —$(CH_2)_m$—$R^5$ (where m is 1–8), $CH_2SCH_3$ or a $C_4$–$C_8$ alkyl bonded to said nitrogen and one of its adjacent carbon atoms inclusive to form a cyclic structure;

$R^4$ is independently hydrogen, $CF_3$, $CH_2CF_3$, $C_1$–$C_8$ alkyl, $C_3$–$C_8$ cycloalkyl, $C_4$–$C_9$cycloalkyl-methyl, $C_2$–$C_8$ alkenyl, $C_2$–$C_8$ alkynyl, 3,3,3-trifluoropropyl, 4,4,4-trifluorobutyl, —$(CH_2)_m$—$R^5$ where m is 1–8;

$R^5$ is phenyl, phenyl (substituted with a CN, $CF_3$, $CH_2CF_3$, $C_1$–$C_8$ alkyl, $C_3$–$C_8$ cycloalkyl, $C_4$–$C_9$ cycloalkyl-methyl, $C_2$–$C_8$ alkenyl, $C_2$–$C_8$ alkynyl), 2-thiophenyl, 3-thiophenyl, —$NR^6CONR^6R^7$, or —$CONR^6R^7$:

$R^6$ and $R^7$ are independently hydrogen, $C_1$–$C_8$ alkyl, $C_3$–$C_8$ cycloalkyl, $C_4$–$C_9$ cycloalkyl, methyl, $C_2$–$C_8$ alkenyl or $C_2$–$C_8$ alkynyl; and with the proviso that when $R^1$ is 2-CN or 4-CN, $R^2$ is H, $R^3$ is n-Pr and n is 1 or 3 then such compound is a pure enantiomer.

Preferred compounds of formula (B) include (3S)-3-[3-(Methylsulfonyl)phenyl]-1-propylpiperidine hydrochloride, (3S)-3-[3-(Methylsulfonyl)phenyl]-1-propylpiperidine hydrobromide, and (3S)-3-[3-Methylsulfonyl)phenyl]-1-propylpiperidine (2E)-2-butenedioate (1:1).

Further disclosed is a method of treating symptoms of fibromyalgia syndrome or chronic fatigue syndrome which comprises administering to a patient in need of treatment a therapeutically effective amount of a cabergoline-type compound, or pharmaceutically acceptable salts thereof, with the preferred compound of this class being cabergoline.

DETAILED DESCRIPTION OF THE INVENTION

The present invention relates to therapies for fibromyalgia (FMS) and chronic fatigue syndrome (CFS), and more particularly to the use of three broad classes of compounds having dopamine receptor activities for treating the symptoms of FMS and CFS. The useful compounds identified for the method of the present invention are described in two ways, with generic descriptions of completely enabled and disclosed groups of compounds and with detailed individually described compound structures and names. One class of compounds useful for treating symptoms of CFS and FMS in the present invention are those compounds, or pharmaceutically acceptable salts thereof, di-closed generically or specifically in U.S. Pat. Nos. 5,273,975 and 5,436,240. These compounds are generically referred to as heterocyclic amine type compounds and are structurally represented by formula (A),

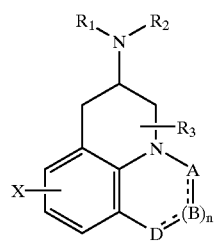

Formula (A)

wherein:

$R_1$, $R_2$, and $R_3$ are independently and are hydrogen, $C_{1-6}$ alkyl, $C_{3-5}$alkenyl, or $C_{3-5}$ alkynyl, $C_{3-7}$ cycloalkyl, $C_{4-10}$ cycloalkyl- or phenyl-substituted $C_{1-6}$ alkyl, or $R_1$ and $R_2$ are joined to form a $C_{3-7}$ cyclic amine which can contain additional heteroatoms and/or unsaturation;

X is hydrogen, $C_{1-6}$ alkyl, halogen, hydroxy, alkoxy, cyano, carboxamide, carboxyl, or carboalkoxyl;

A is CH, $CH_2$, CH-halogen, $CHCH_3$, C=O, C=S, C—$SCH_3$, C=NH, C—$NH_2$, C—$NHCH_3$, C—$NHCOOCH_3$, or C—NHCN, $SO_2$, or N;

B is $CH_2$, CH, CH-halogen, C=O, N, NH, N—$CH_3$ or O;

n is 0 or 1; and

D is CH, $CH_2$, CH-halogen, C=O, O, N, NH or N—$CH_3$.

The methods oft making the compounds and the pharmaceutically preparations are described in U.S. Pat. Nos. 5,273,975 and 5,436,240, and in International Patent Application WO 00/40226. The full disclosure of the above-cited U.S. Pat. Nos. 5,273,975 and 5,436,240 and International Patent Application WO 00/40226 is incorporated herein by reference.

An especially preferred compound of formula (A) in the present invention is a compound of formula (Aa),

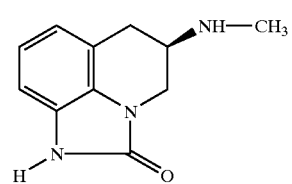

Formula (Aa)

or pharmaceutically acceptable salt thereof. The compound name for the compound of formula (Aa) is (R)-5,6-Dihydro-5-(methylamino)-4H-imidazo[4,5,1-ij]-quinolin-2(1H)-one (uninverted CAS name) or (5R)-5-(methylamino)-5,6-dihydro-4H-imidazo[4,5,1-ij]quinolin-2(1H)-one (Generated by ACD/Name software).

It is preferred that (R)-5,6-Dihydro-5-(methylamino)-4H-imidazo[4,5,1-ij]-quinolin-2(1H)-one be present in a pharmaceutically acceptable salt. Suitable pharmaceutically acceptable salts include salts of both inorganic and organic acids; examples include without limitation salts of the following acids: hydrochloric, hydrobromic, sulfuric, phosphoric, nitric, citric, methanesulfonic, $CH_3$—$(CH_2)_{n1}$—COOH where $n_1$ is 0 thru 4, HOOC—$(CH_2)n_1$—COOH where n is as defined above, HOOC—CH=CH—COOH, and $\phi$—COOH. For other acceptable salts, see Int. J. Pharm., 33, 201–217 (1986). A particularly preferred salt of (R)-5,6-Dihydro-5-(methylamino)-4H-imidazo[4,5,1-ij]-quinolin-2(1H)-one is the maleate, i.e. (Z)-2-butenedioate, salt, which is (R)-5,6-Dihydro-5-(methylamino)-4H-imidazo[4,5,1-ij]-quinolin-2(1H)-one (Z)-2-butenedioate (1:1). The (Z)-2-butenedioate salt is shown as formula (Ab):

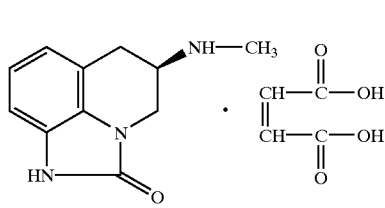

Formula (Ab)

Another group of compounds within the generic formula of the heterocyclic amine-type compounds shown above, are selected heterocyclic amine compounds, the most preferred being (5R)-5-(methylamino)-5,6-dihydro-4H-imidazo[4,5,1-ij]quinoline-2(1H)-thione, a compound of the formula (Ac) below, also referred to herein at formula (VIII),

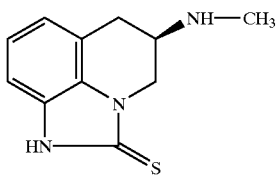

Formula (Ac) or (VIII)

or pharmaceutically acceptable salts thereof.

U.S. Pat. No. 5,273,975 generically discloses and claims (5R)-5-(methylamino)-5,6-dihydro-4H-imidazo[4,5,1-ij] quinoline-2(1H)-thione, but does not give an example or specific mention of this compound. (5R)-5-(methylamino)-5,6-dihydro-4H-imidazo[4,5,1-ij]quinoline-2(1H)-thione (VIII) is preferably made from the corresponding non-thio analog, (5R)-(methylamino)-5,6-dihydro-4H-imidao(4,5,1-ij)quinolin-(2H)-one (VII). A preferred process of making (5R)-(Methylamino)-5,6-dihydro-4H-imidao(4,5,1-ij)quinolin-(2H)-one (VII) is illustrated in PREPARATION 1 and EXAMPLEs 1–6, as well as CHART A. The preferred method of transforming (5R)-(methylamino)-5,6-dihydro-4H-imidao(4,5,1-ij)quinolin-(2H)-one (VII) into (5R)-5-(methylamino)-5,6-dihydro-4H-imidazo[4,5,1-ij]quinoline-2(1H)-thione (VIII) is set forth in EXAMPLE 8.

It is prepared that (5R)-5-(methylamino)-5,6-dihydro-4H-imidazo[4,5,1-ij]quinoline-2(1H)-thione (IX) be present as a pharmaceutically acceptable salt. Pharmaceutically acceptable salts include salts of both inorganic and organic acids. The preferred pharmaceutically acceptable salts include salts of the following acids hydrochloric, hydrobromic, sulfuric, phosphoric, nitric, citric, methanesulfonic $CH_3$—$(CH_2)_{n1}$—COOH where $n_1$ is 0 thru 4, HOOC—$(CH_2)n_1$—COOH where n is as defined above, HOOC—CH=CH—COOH, $\phi$—COOH. For other acceptable salts, see *Int. J. Pharm.*, 33, 201–217 (1986). It is more preferred that (5R)-5-(methylamino)-5,6-dihydro-4H-imidazo[4,5,1-ij] quinoline-2(1H)-thione be present as the maleate salt, which is (5R)-5-(methylamino)-5,6-dihydro-4H-imidazo[4,5,1-ij] quinoline-2(1H)-thione maleate. The maleate salt is shown below as formula (Ad) or formula (IX):

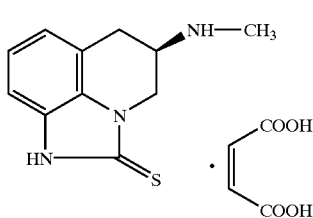

Formula (Ad) or (IX)

Conventional pharmaceutical preparations can be used for the heterocyclic amine-type compounds, e.g., consisting essentially of an inert pharmaceutical carrier and an effective dose of the active substance. Suitable dosages forms include without limitation plain or coated tablets, capsules, lozenges, powders, solutions, suspensions, emulsions, syrups, suppositories, transdermal patch, etc, with tablet being the preferred dosage form.

The effective dose range for oral administration of a heterocyclic amine-type compound is from about 0.30 through about 50.0 mg/dose/patient orally. Patients with milder forms of FMS or CFS would be expected to need less drug, while patients with more severe forms of the disease may be expected to need more drug. The dosages to be given to a particular patient should be easily determined by a skilled physician with experience in prescribing biologically active drugs designed to modulate central nervous system, movement and related psychological and physiological disorders of the type described here. Normally the drug is given once a day or twice a day, it may be given even less often for some patients.

Another class of compounds useful in the present invention are those compounds, or pharmaceutically acceptable salts thereof, disclosed generically or specifically in U.S. Pat. Nos. 5,594,024 and 5,462,947, both incorporated by reference herein. These compounds are generically referred to as substituted phenylazacycloalkane-type compounds and are structurally represented by formula (B),

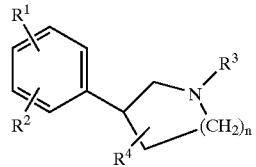

Formula (B)

wherein:

n is 0–3;

$R^1$ and $R^2$ are independently H (provided only one is H at the same time), —OH (provided $R^4$ is other than hydrogen), CN, $CH_2CN$, 2- or $4CF_3$, $CH_2$-$CF_3$, $CH_2CHF_2$, CH=$CF_2$, $(CH_2)_2CF_3$, ethenyl, 2-propenyl, $OSO_2CH_3$, $OSO_2CF_3$, $SSO_2CF_3$, $COR^4$, $COOR^4$, CON $(R^4)_2$, $SO_xCH_3$ (where, x is 0–2), $SO_xCF_3$, $O(CH_2)_x$ $CF_3$, $SO_2N(R^4)_2$, CH=$NOR^4$, $COCOOR^4$, COCOON $(R^4)_2$, $C_{1-8}$ alkyls, $C_{3-8}$ cycloalkyls, $CH_2OR^4$, $CH_2(R^4)_2$, $NR^4SO_2CF_3$, $NO_2$, halogen, a phenyl at positions 2, 3 or 4, thienyl, furyl, pyrrole, oxazole, thiazole, N-pyrroline, triazole, tetrazole or pyridine;

$R^3$ is hydrogen, $CF_3$, $CH_2CF_3$, $C_1$–$C_8$ alkyl, $C_3$–$C_8$ cycloalkyl, $C_4$–$C_9$ cycloalkyl-methyl, $C_2$–$C_8$ alkenyl, $C_2$–$C_8$ alkynyl, 3,3,3-trifluoropropyl, 4,4,4-trifluorobutyl, —$(CH_2)_m$—$R^5$(where m is 1–8), $CH_2SCH_3$ or a $C_4$–$C_8$ alkyl bonded to said nitrogen and one of its adjacent carbon atoms inclusive to form a cyclic structure;

$R^4$ is independently hydrogen, $CF_3$, $CH_2CF_3$, $C_1$–$C_8$ alkyl, $C_3$–$C_8$ cycloalkyl, $C_4$–$C_9$cycloalkyl-methyl, $C_2$–$C_8$ alkenyl, $C_2$–$C_8$ alkynyl, 3,3,3-trifluoropropyl, 4,4,4-trifluorobutyl, —$(CH_2)_m$—$R^5$ where m is 1–8;

$R^5$ is phenyl, phenyl (substituted with a CN, $CF_3$, $CH_2CF_3$, $C_1$–$C_8$ alkyl, $C_3$–$C_8$ cycloalkyl, $C_4$–$C_9$ cycloalkyl-methyl, $C_2$–$C_8$ alkenyl, $C_2$–$C_8$ alkynyl), 2-thiophenyl, 3-thiophenyl, —$NR^6CONR^6R^7$, or —$CONR^6R^7$;

$R^6$ and $R^7$ are independently hydrogen, $C_1$–$C_8$ alkyl, $C_3$–$C_8$ cycloalkyl, $C_4$–$C_9$ cycloalkyl-methyl $C_2$–$C_8$ alkenyl or $C_2$–$C_8$ alkynyl; and with the proviso that when $R^1$ is 2-CN or 4-CN, $R^2$ is H, $R^3$ is n-Pr and n is 1 or 3 then such compound is a pure enantiomer.

Also useful in the present invention are pharmaceutically acceptable salts of compounds of formula (B), those salts being disclosed in U.S. Pat. Nos. 5,462,947 and 5,594,024, both incorporated herein by reference. Both organic and inorganic acids can be employed to form pharmaceutically acceptable salts; illustrative acids include sulfuric, nitric, phosphoric, hydrochloric, citric, acetic, lactic, ethanedisulfonic, sulfamic, succinic, cyclohexylsulfamic, fumaric, maleic, and benzoic acids. These salts are readily prepared by methods known in the art.

A particularly suitable compound of formula (B) in the present invention is (3S)-3-[3-(Methylsulfonyl)phenyl]-1-propylpiperidine hydrochloride (uninverted CAS name) or OSU 6162 or (3S)-3-[3-(methylsulfonyl)phenyl]-1-propylpiperidine hydrochloride (Generated by ACD/Name software), and is represented by formula (Ba):

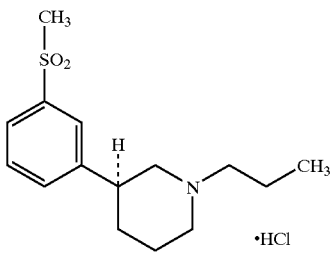

Formula (Ba)

Another particularly suitable compound of formula (B) in the present invention is (3S)-3-[3-(Methylsulfonyl)phenyl]-1-propylpiperidine hydrobromide (uninverted CAS name) or (3S)-3-[3-(methylsulfonyl)phenyl]-1-propylpiperidine hydrobromide (Generated by ACD/Name software), and is represented by formula (Bb):

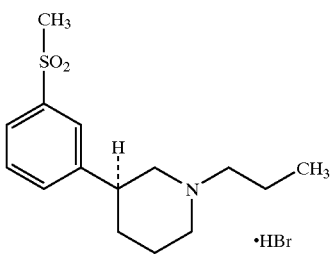

Formula (Bb)

Yet another particularly suitable compound of formula (B) in the present invention is (3S)-3-[3-Methylsulfonyl)phenyl]-1-propylpiperidine (2E)-2-butenedioate (1:1) (uninverted CAS name) or (S)-OSU6162, and is represented by formula (Bc):

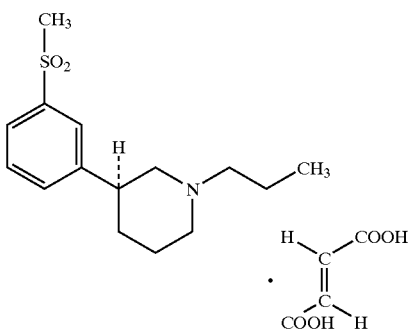

Formula (Bc)

The methods of preparing these compounds, and formulations and medicaments of the same, are described in U.S. Pat. Nos. 5,594,024 and 5,462,947, both incorporated herein by reference.

Conventional pharmaceutical preparations can be used for the substituted phenylazacycloalkane-type compounds, e.g., consisting essentially of an inert pharmaceutical carrier and an effective dose of the active substance; e.g., plain or coated tablets, capsules, lozenges, powders, solutions, suspensions, emulsions, syrups, suppositories, transdermal patch, etc. Preferred dosage forms are tablets.

The effective dose range for oral administration of a substituted phenylazacycloalkane-type compound is from about 10 to about 1000 mg/dose/patient once or twice a day. The dosage and dose frequency for a particular patient should be easily determined by a skilled physician with experience in prescribing biologically active drugs designed to modulate central nervous system, movement and related psychological and physiological disorders of the type described here. While normally the drug may be given once a day or twice a day, it may be given even less often for some patients.

A further class of compounds useful in the present invention are those compounds, or pharmaceutically acceptable salts thereof, disclosed generically or specifically in U.S. Pat. No. 4,526,892, the full disclosure of which is incorporated herein by reference. These compounds are generically referred to as cabergoline-type compounds. The preferred compound in this class is cabergoline itself, or its pharmaceutically acceptable salts. The chemical name for cabergoline is 1-((6-allylergolin-8β-yl)-carbony.)-1-(3-(dimethylamino)propyl)-3-ethylurea and the structure of carbergoline is represented by formula (C):

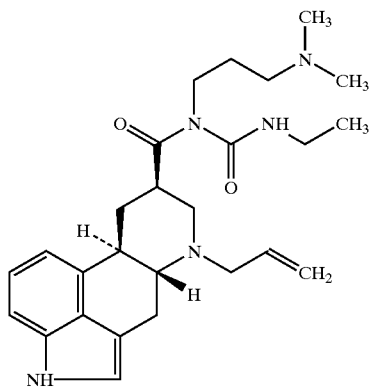

Formula (C)

Cabergoline is the generic name for the active ingredient in DOSTFNEX® or CABASER® Tablets, which are marketed by Pharmacia & Upjohn, Inc. in the United States, Europe and Latin America as a treatment for hyperprolactinemic disorders and Parkinson's disease. The synthesis and use of cabergoline is disclosed and claimed in U.S. Pat. No. 4,526,892, which is incorporated here-in by reference.

Conventional pharmaceutical preparations can be used for cabergoline, e.g., consisting essentially of an inert pharmaceutical carrier and an effective dose of the active substance, e.g., plain or coated tablets, capsules, lozenges, powders, solutions, suspensions, emulsions, syrups, suppositories, etc, with tablet being the preferred dosage form.

A package insert describing CABASER®, its pharmacokinetics, clinical studies, indications and usage, contraindication and warnings, and Parkinson's disease patients is provided by Pharmacia & Upjohn, Inc. This package insert and its descriptions are incorporated by reference into this application.

The effective dose range for cabergoline is from about 0.01 to about 10.0 mg/dose/patient, preferably from about 0.25 to about 10.0 mg/dose/patient, more preferably from about 1 to about 6 mg/dose/patient, and even more preferably from about 1 to about 2 mg/dose/patient orally. At these dose levels above, cabergoline is typically administered once or twice a day; however, for some patients the dose frequency may be reduced to three times a week, two times a week or even once a week. The combination of dosage levels and dose frequency for a particular patient may be readily adjusted by the treating physician.

The dose response to cabergoline in terms of efficacy and side effects appears to be mainly linked to individual sensitivity. Under some circumstances and with the appropriate patients, dose optimization may be obtained, for example, by administering a low initial dose of cabergoline to the patient at a dose of 0.5 to 1 mg/patient/day and adjusting the dose upward at weekly intervals to an optimal therapeutic dosage of 2, 4, 6, 8 or 10 mg/patient/day. Patients with milder forms of the disease would be expected to need less drug. For example, in some cases a dose of 0.05, 0.1 or even 0.25 mg/patient may be adequate. Patients with more severe forms of the disease and those who have been treated with other dopaminergic agents may be expected to need more drug. The precise dosage would be readily determined by the treating physician evaluating such factors as the progression of the state of the disease, the weight and age of the patient, whether and to what extent other drugs such as L-Dopa or levodopa were administered, and other such factors as are typically evaluated by a physician before determining the dosage of a CNS drug to a patient.

Definitions and Convention

The definitions and explanations below are for the terms as used throughout this entire document including both the specification and the claims.

Definitions

All temperatures are in degrees Celsius.

TLC refers to thin-layer chromatography.

HPLC refers to high pressure liquid chromatography.

Saline refers to an aqueous saturated sodium chloride solution.

Chromatography (column and flash chromatography) refers to purification/separation of compounds expressed as (support, eluent). It is understood that the appropriate fractions are pooled and concentrated to give the desired compound(s).

IR refers to infrared spectroscopy.

CMR refers to C-13 magnetic resonance spectroscopy, chemical shifts are reported in ppm ($\delta$) downfield from TMS.

NMR refers to nuclear (proton) magnetic resonance spectroscopy, chemical shifts are reported in ppm ($\delta$) downfield from tetramethylsilane.

$\phi$ refers to phenyl ($C_6H_5$).

$[\alpha]_D^{25}$ refers to the angle of rotation of plane polarized light (specific optical rotation) at 25° with the sodium D line (589A).

MS refers to mass spectrometry expressed as m/e, m/z or mass/charge unit. $[M+H]^+$ refers to the positive ion of a parent plus a hydrogen atom. EI refers to electron impact. CI refers to chemical ionization. FAB refers to fast atom bombardment.

Pharmaceutically acceptable refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability.

When solvent pairs are used, the ratios of solvents used are volume/volume (v/v).

When the solubility of a solid in a solvent is used the ratio of the solid to the solvent is weight/volume (wt/v).

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

PREPARATION 1 (R)-Naproxen Chloride R-naproxen (Can. J. Chem., 72(1), 142–5 (1994), 260 g), methylene chloride (3.33 kg) and DMF (8.2 ml) are added to a reactor. Oxalyl chloride (191.8 g) is slowly added to this mixture. After addition of the oxalyl chloride, the slurry is stirred at 5 to 10° and then slowly warmed to 20–25°. The resulting mixture is concentrated to remove the methylene chloride, branched octane is added to the concentrate and the mixture is again concentrated. More branched octane is added to the concentrate and the mixture is cooled to 0° and stirred to crystallize. The crystal slurry is filtered, the crystal cake is washed with octane and dried at 20–25° to obtain the title compound.

The filtrate from the first crop is concentrated, branched octane is added and the mixture is cooled and stirred to obtain a second crop of the title compound. The slurry is filtered, the crystal cake is washed with branched octane and dried at 20–25°.

Example 1

1-Benzyl-4H-imidazo[4,5,1-ij]quinolin-2(1H)-one (II)

A mixture of 4H-imidazo[4,5,1-ij]quinolin-2(1H)-one (I, J. Heterocyclic Chem., 19, 837–49 (1982), 1.0 g, 5.8 mmol) in DMF (10 ml) is cooled to 0° and treated with potassium t-butoxide in THF (1.98 M, 3.2 ml, 6.3 mmol) maintaining the reaction temperature at 0°. The resulting mixture is stirred at 0° for 10 minutes. Benzyl bromide (0.73 ml, 6.1 mmol) is then added while maintaining the reaction temperature at methyl t-butyl ether (MTBE) from water followed by several water washes. The MTBE phase is concentrated under reduced pressure. The concentrate is cooled to 0°, filtered and washed two times with 0° MTBE. The product is dried at 50° under reduced pressure with a nitrogen purge to give the title compound, CMR ($CDCl_3$, 100 MHz) 153.78, 136.44, 128.69, 127.67, 127.60, 126.73, 125.86, 122.90, 122.78, 121.28, 116.92, 116.17, 108.36, 44.95 and 42.37 $\delta$.

Example 2

(5R,6R)-1-Benzyl-5-bromo-6-hydroxy-5,6-dihydro-4H-imidazo[4,5,1-ij]quinolin-2(1H)-one (III)

1-Benzyl-4H-imidazo[4,5,1-ij]quinolin-2(1H)-one (II, EXAMPLE 1, 240 g), acetonitrile (1.086 kg), water (227 ml) and fluoboric acid (48.5%, 13.4 g) are mixed and cooled to 0 to 5°. Dibromantin (163.5 g) is slurried into acetonitrile and is added to the reaction mixture. The reaction is carried out for about 3 hr at 0 to 5°. After the reaction is complete, methyl t-butyl ether is added over about 45 minutes keeping the reaction temperature in the pot below 10°. The slurry is cooled to −10 to −15°, stirred for an hour and then filtered. The product is washed with precooled methyl t-butyl ether, dried with 40° nitrogen to give the title compound, CMR ($CDCl_3$) 156.0, 137.8, 130.5, 129.6, 129.3, 129.1, 126.6, 123.6, 122.5, 119.6, 110.4, 69.9, 49.6, 47.7, 46.9 and 43.8 $\delta$.

Example 3

(5S,6S)-1-Benzyl-5-bromo-2oxo1,2,5, 6tetrahydro4Himidazo[4,5,1ij]quinolin6yl(2R)-6-methoxy-2-naphthyl)propanoate (IVA) and (5R,6R)-1-benzyl-5-bromo-2-oxo -1,2,5,6-tetrahydro-4H-imidazo[4,5,1-ij]quinolin-6-yl (2R)-(6-methoxy-2-naphthyl)propanoate (IVB)

(5R,6R)-1-Benzyl-5-bromo-6-hydroxy-5,6-dihydro-4H-imidazo[4,5,1-ij]quinolin-2(1H)-one (III, EXAMPLE 2, 143 g), methylene chloride (3, 136 g), N-methyl morpholine (100.2 g) and 4-dimethylaminopyridine (497 mg) are added to the reactor and the mixture is cooled to 0 to 5°. (R)-Naproxen chloride (PREPARATION 1, 118.5 g) dissolved in methylene chloride (694 ml) is added to the reactor over about 1 hr and the mixture is stirred at 0 to 5° to complete the reaction. If necessary, additional naproxen chloride is added to complete the reaction. Potassium carbonate solution diluted with water is added to the mixture. The aqueous phase is extracted with methylene chloride and the combined methylene chloride phase is washed with water. The washed mixture is concentrated by vacuum distillation and solvent exchange with ethyl acetate is performed. The concentrate is cooled to −10° and stirred. The crystal slurry is filtered and the crystal cake is washed with precooled methyl t-butyl ether and dried at 50° to give the title compound in solid form, (5S,6S)-1-benzyl-5-bromo-2-oxo-1,2,5,6-tetrahydro-4H-imidazo[4,5,1-ij]quinolin-6-yl (2R)-2-(6-methoxy-2-naphthyl)propanoate (IVA), CMR (CDCl$_3$) δ 173.2, 157.8, 153.4, 136.1, 134.6, 133.7, 129.2, 128.8, 127.8, 127.8, 127.6, 127.2, 125.9, 125.9, 125.6, 121.5, 121.4, 119.1, 113.2, 109.0, 105, 105.6, 69.2, 55.3, 45.4, 45.2, 42.5, 41.7 and 18.3.

The undesired isomer, (5R,6R)-1-benzyl-5-bromo-2-oxo-1,2,5,6-tetrahydro-4H-imidazo[4,5,1-ij]quinolin-6-yl (2R)-2-(6-methoxy-2-naphthyl)propanoate (IVB) is in the filtrate and can be recovered by means well known to those skilled in the art, (5R,6R)-1-benzyl-5-hydroxy-6-(methylamino)-5,6-dihydro-4H-imidazo[4,5,1-ij]quinolin-2(1H)-one, CMR (CDCl$_3$) δ 173.2, 157.9, 153.4, 136.1, 135.0, 133.8, 129.2, 128.9, 128.8, 127.8, 127.6, 127.4, 125.8, 125.8, 125.7, 121.6, 121.5, 119.3, 113.1, 109.1, 105.7, 68.7, 55.3, 45.3, 45.2, 42.2, 41.3 and 18.1.

Example 4

(5R,6R)-1-Benzyl-5-hydroxy-6-(methylamino)-5,6-dihydro-4H-imidazo[4,5,1-ij]quinolin-2(1H)-one (V)

(5S,6S)-1-Benzyl-5-bromo-2-oxo-1,2,5,6-tetrahydro-4H-imidazo[4,5,1-ij]quinolin-6-yl (2R)-2-(6-methoxy-2-naphthyl)propanoate (IVA, EXAMPLE 3, 110 g) is slurried in acetonitrile (1,297 g). After adding aqueous methylamine (40 wt %, 327 g) the reaction is carried out for about 12 hr at about 30°. After the reaction is complete, the mixture is concentrated and ethyl acetate is added. Dilute hydrochloric acid is added to make the water-soluble salt of the title compound. The byproduct (R-naproxen methylamide impurity) is insoluble in water and stays in the ethyl acetate phase. Further extractions and washes are carried out for better separation of the (naproxen acetamide) impurity with minimum loss of the desired product. Then a sodium hydroxide solution is added to the aqueous phase and the hydrochloride salt of the title compound is converted to the free base. The free base is less soluble in water and is extracted into ethyl acetate. The product mixture is concentrated and solvent exchanged with ethyl acetate to remove water. Crystallization is performed by adding branched chain octane and cooling the mixture. The resulting slurry is filtered, washed and dried at 50° to give the title compound, CMR (CDCl$_3$) δ 153.7, 136.3, 128.7, 127.8, 127.7, 125.7, 121.3, 119.9, 118.6, 107.5, 66.2, 60.1, 45.1, 42.6 and 34.0.

Example 5

(7aS,8aR)-4-Benzyl-8-methyl-7,7a,8,8a-tetrahydroazireno[2,3-c]imidazo[4,5,1-ij]quinolin-5(4H)-one (VI)

(5R,6R)-1-Benzyl-5-hydroxy-6-(methylamino)-5,6-dihydro-4H-imidazo[4,5,1-ij]quinolin-2(1H)-one (V, EXAMPLE 4, 70 g) and THF (1,389 g) is concentrated to remove any by distillation as a precaution due to reactivity of n-butyllithium towards water. The mixture is cooled to about −10° and n-butyllithium is added to make the lithium salt of the starting material with formation of n-butane byproduct in an exothermic reaction. Benzenesulfonyl chloride is added slowly to make benzenesulfonate in an exothermic reaction. The reaction mixture is warmed to 20–25° to complete the reaction. Agueous potassium carbonate solution is added to scavenge the benzenesulfonic acid and the mixture is stirred to allow crystallization. Water is added to complete crystallization, the slurry is stirred, cooled and filtered. The crystal cake is washed with water followed by branched chain octane and dried at 40 to 50° to give the title compound, CMR (CDCl$_3$) δ 154.1, 136.3, 128.6, 127.9, 127.6, 124.3, 120.7, 119.7, 107.4, 46.7, 44.9, 40.7, 38.1 and 37.6.

Example 6

(5R)-(Methylamino)-5,6-dihydro-4H-imidazo[4,5,1-ij]quinolin-2(1H)-one (VII)

A mixture of (7aS,8aR)-4-benzyl-8-methyl-7,7a,8,8a-tetrahydroazireno[2,3-c]imidazo[4,5,1-ij]quinolin-5(4H)-one (VI, EXAMPLE 5, 40 g) t-amyl alcohol (42.4 g) and anhydrous ammonia (1,200 g) is treated with lithium at −33°. After the lithium addition is complete, the reaction mixture changes from a yellow slurry to a dark blue mixture. This dark blue mixture is stirred for 30–60 minutes and then quenched with the addition of water. The cooling is removed from the condenser and the ammonia is allowed to evaporate. The residue is dissolved in methanol. This mixture is then concentrated to dryness to give the title compound, which is carried on directly to the next step without isolation.

Example 7

(5R)-5-(Methylamino)-5,6-dihydro-4H-imidazo[4,5,1-ij]quinoline-2(1H)-thione (VIII)

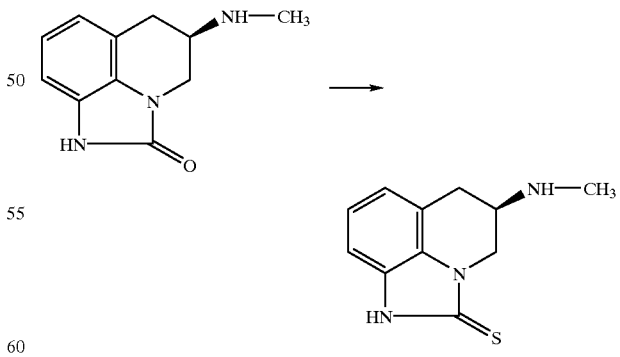

A mixture of (5R)-(methylamino)-5,6-dihydro-4H-imidazo[4,5,1-ij]quinolin-2(1H)-one (VII, EXAMPLE 6, 15.0 g, 73.8 mmol) and tetraphosphorus decasulfide (36.1 g, 81.2 mmol) in pyridine (300 mL) is heated in a 125° oil bath under nitrogen. The reaction is stirred for 5 hr. The mixture is cooled to 20–25° and the pyridine is removed under reduced pressure. Sodium hydroxide (2.2 N, 200 mL) is added and a vigorous reaction ensues. Additional sodium hydroxide (1 N) is added until a solution is formed. The solution is saturated with sodium chloride and extracted with methylene chloride (2.5 L, in portions). The organic phase is absorbed onto silicon dioxide (40 g) and purified via column chromatography (silicon dioxide, 225 g; methanol/methylene chloride, 3.5–5.0/96.5–95). The appropriate fractions are pooled and concentrated. The material is recrystallized from methanol/ethyl acetate/hexanes to give the title compound, mp=210–213°; IR (drift) 2940, 2907, 2884, 1483, 1458, 1391, 1366, 1354, 1254, 1239, 1229, 895, 762, 734 and 630 cm$^{-1}$; NMR (300 MHz, CDCl$_3$) δ 7.12, 7.03, 7.00, 4.30, 3.96, 3.30–3.50, 3.15, 2.88 and 2.57; MS (EI) m/z 219 (M$^+$), 190, 189, 187, 186, 164, 163, 155, 145; HRMS (FAB) calculated for C$_{11}$H$_{13}$N$_3$S (MH$^+$)=220.0908, found=220.0904.

Example 8

(5R)-5-(Methylamino)-5,6-dihydro-4H-imidazo[4,5,1-ij]quinoline-2(1H)-thione maleate(IX)

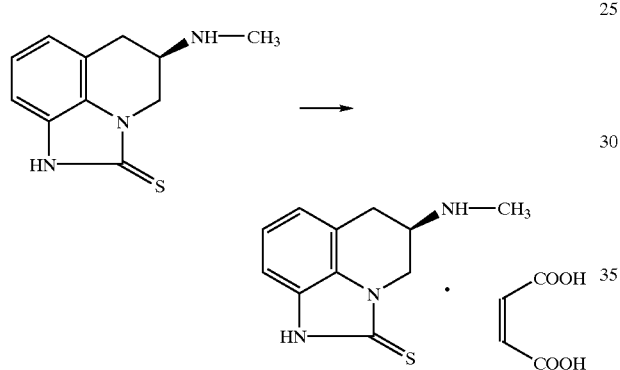

A solution of maleic acid (0.317 g, 2.36 mmol) in a minimal amount of methanol (~1 mL) is added to a mixture of (5R)-5-(methylamino)-5,6-dihydro-4H-imidazo[4,5,1-ij]quinoline-2(1H)-thione (VIII, EXAMPLE 7, 0.493 g, 2.25 mmol) in methylene chloride. The resulting solid is collected by filtration to give the title compound; mp=195–196°; [α]$^{25}$D=–60° (c 0.93, methanol); IR (drift) 3140, 3112, 3060, 2969, 1627, 1619, 1568, 1481, 1455, 1398, 1389, 1361, 1220, 868 and 747 cm$^{-1}$; NMR (300 MHz, CD$_3$OD) δ 7.20–7.30, 7.10–7.20, 6.26, 4.49, 4.31, 4.05–4.20, 3.28 and 2.83; CMR (100 MHz, DMSO-d$_6$+CD$_3$OD) δ 170.4, 169.4, 136.6, 131.1, 130.9, 125.1, 122.1, 116.2, 109.6, 53.9, 43.1, 31.9 and 27.2; MS (ESI) m/z=220.1 (MH$^+$).

CHART A

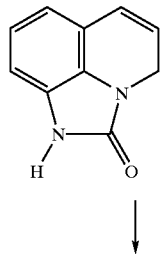

(I)

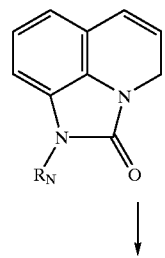

(II)

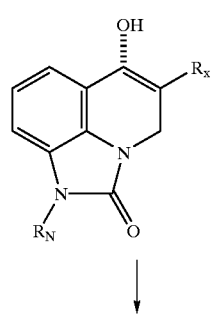

(III)

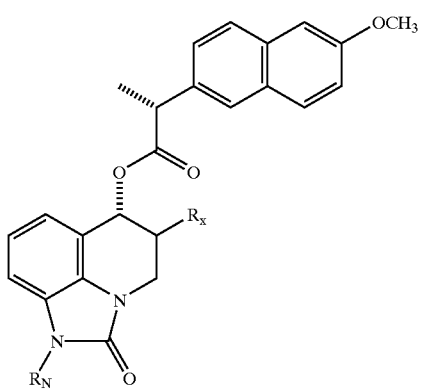

(IV)

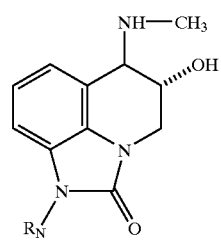

(V)

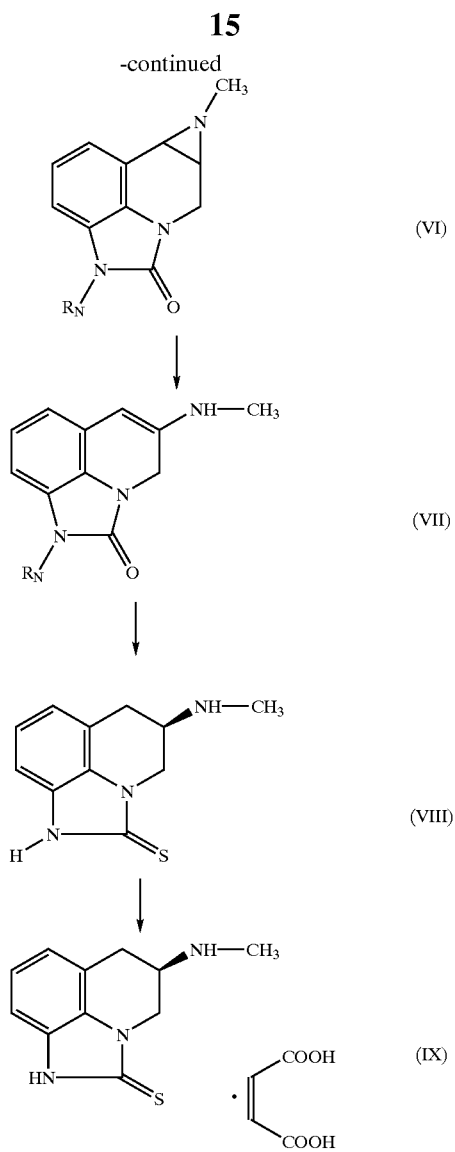

What is claimed is:

1. A method of treating the symptoms of fibromyalgia syndrome or chronic fatigue syndrome, comprising administering to a patient in need of treatment a therapeutically effective amount of an active agent selected from the group consisting of a cabergoline-type compound and pharmaceutically acceptable salts of said compound.

2. The method of claim 1 wherein said cabergoline-type compound is 1-((6-allylergolin-8β-yl)-carbony)-1-(3-(dimethylamino)propyl)-3-ethylurea.

3. The method of claim 1 wherein said cabergoline-type compound is cabergoline, or a pharmaceutically acceptable salt thereof.

4. The method of claim 1 wherein said active agent is a cabergoline-type compound of formula (C),

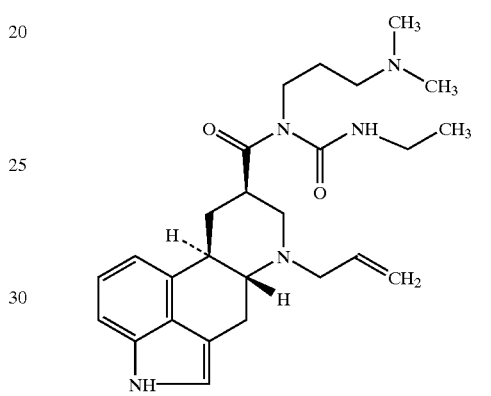

or a pharmaceutically acceptable salt thereof.

* * * * *